(12) United States Patent
Ahmed et al.

(10) Patent No.: US 7,579,402 B2
(45) Date of Patent: Aug. 25, 2009

(54) SUPERABSORBENT POLYMER HAVING DELAYED FREE WATER ABSORPTION

(75) Inventors: Iqbal Ahmed, Greensboro, NC (US); Angela Marie Jones, Burlington, NC (US); Scott J. Smith, Greensboro, NC (US)

(73) Assignee: Evonik Stockhausen, Inc., Greensboro, NC (US)

( * ) Notice: Subject to any disclaimer, the term of this patent is extended or adjusted under 35 U.S.C. 154(b) by 0 days.

(21) Appl. No.: 10/706,569

(22) Filed: Nov. 12, 2003

(65) Prior Publication Data

US 2006/0173097 A1    Aug. 3, 2006

(51) Int. Cl.
*B32B 27/30* (2006.01)
*B32B 27/18* (2006.01)
*C08L 33/08* (2006.01)

(52) U.S. Cl. .............. 524/560; 428/436; 428/437; 428/402; 428/401

(58) Field of Classification Search .......... 524/560, 524/437, 436, 434; 523/200; 428/402, 403
See application file for complete search history.

(56) References Cited

U.S. PATENT DOCUMENTS

| | | | | |
|---|---|---|---|---|
| 4,043,952 A * | 8/1977 | Ganslaw et al. | ............. | 524/399 |
| 4,548,847 A * | 10/1985 | Aberson et al. | ............. | 428/74 |
| 4,605,401 A | 8/1986 | Chmelir et al. | | |
| 5,002,986 A * | 3/1991 | Fujiura et al. | ............. | 524/47 |
| 5,115,011 A * | 5/1992 | Harada et al. | ............. | 524/419 |
| 5,338,766 A * | 8/1994 | Phan et al. | ............. | 521/63 |
| 5,684,106 A * | 11/1997 | Johnson et al. | ............. | 526/295 |
| 5,855,571 A | 1/1999 | Steger et al. | | |
| 6,323,252 B1 * | 11/2001 | Gartner et al. | ............. | 521/149 |
| 6,433,058 B1 * | 8/2002 | Weir et al. | ............. | 524/431 |
| 6,514,615 B1 * | 2/2003 | Sun et al. | ............. | 428/402 |
| 6,562,743 B1 * | 5/2003 | Cook et al. | ............. | 442/409 |
| 6,579,958 B2 * | 6/2003 | Wilson | ............. | 526/185 |
| 6,620,889 B1 * | 9/2003 | Mertens et al. | ............. | 525/221 |
| 6,696,618 B2 * | 2/2004 | Dodge et al. | ............. | 604/367 |
| 7,157,141 B2 * | 1/2007 | Inger et al. | ............. | 428/403 |
| 7,241,820 B2 * | 7/2007 | Smith et al. | ............. | 524/32 |
| 2002/0193492 A1 | 12/2002 | Wilson | | |
| 2003/0118820 A1 | 6/2003 | Sun et al. | | |
| 2003/0118821 A1 | 6/2003 | Sun et al. | | |
| 2003/0207997 A1 | 11/2003 | Mertens et al. | | |
| 2004/0214499 A1 * | 10/2004 | Qin et al. | ............. | 442/414 |

FOREIGN PATENT DOCUMENTS

| | | |
|---|---|---|
| EP | 0 437 816 A1 | 7/1991 |
| GB | 2 280 115 A | 1/1995 |
| WO | WO 00/53664 A | 9/2000 |
| WO | WO 00/53664 A1 * | 9/2000 |
| WO | WO 01/00258 A | 1/2001 |

OTHER PUBLICATIONS

International Search Report mailed on May 3, 2005 in connection with PCT/US2004/037422.
Written Opinion of the International Searching Authority mailed on May 3, 2005 in connection with PCT/US2004/037422.

* cited by examiner

*Primary Examiner*—David Wu
*Assistant Examiner*—Rip A. Lee
(74) *Attorney, Agent, or Firm*—Smith Moore Leatherwood LLP

(57) ABSTRACT

The present invention is directed to a coated superabsorbent polymer comprising a coated superabsorbent polymer having a delayed free water absorption property of absorbing about 13 grams or less of water per gram of superabsorbent polymer in about 15 seconds. The present invention is directed to a coated superabsorbent polymer having delayed water absorption comprising a) a composition comprising from about 55 to about 99.9 wt. % of polymerizable unsaturated acid group containing monomers; and from about 0.001 to about 5.0 wt. % of internal crosslinking agent; wherein the composition has a degree of neutralization of more than about 20%; and b) a salt coated on the composition.

13 Claims, No Drawings

SUPERABSORBENT POLYMER HAVING DELAYED FREE WATER ABSORPTION

FIELD OF THE INVENTION

The invention relates to superabsorbent polymers which absorb water, aqueous liquids and blood wherein the superabsorbent polymers of the present invention have improved properties, in particular, delayed free water absorption at 15 seconds is enhanced while maintaining acceptable fluid retention properties. The present invention also relates to preparation of these superabsorbent polymers and their use as absorbents in hygiene articles and in industrial fields.

BACKGROUND OF THE INVENTION

Superabsorbent refers to a water-swellable, water-insoluble, organic or inorganic material capable of absorbing at least about 10 times its weight and up to about 30 times its weight in an aqueous solution containing 0.9 weight percent sodium chloride solution in water. A superabsorbent polymer is a crosslinked polymer which is capable of absorbing large amounts of aqueous liquids and body fluids, such as urine or blood, with swelling and the formation of hydrogels, and of retaining them under a certain pressure in accordance with the general definition of superabsorbent.

The superabsorbent polymers that are currently commercially available are crosslinked polyacrylic acids or crosslinked starch-acrylic acid graft polymers, in which some of the carboxyl groups are neutralized with sodium hydroxide solution or potassium hydroxide solution. As a result of these characteristic properties, these polymers are chiefly used for incorporation into sanitary articles, such as babies' diapers, incontinence products or sanitary towels.

In diaper constructions, there is a need to be able to combine the SAP with fibers in a wet laid construction. To this end the SAP needs properties that allow its absorption of water to be delayed for at least 1 minute so as not to react in the construction of the combination of the SAP and fiber in wet laid methods.

GB 2,280,115 A describes an absorbent article, such as diapers, that contains coated superabsorbent particles in the area in which body fluids are released. The coating of the superabsorbent particles prevents swelling until the coating has dissolved in the test or body fluid or has been penetrated by it. These are superabsorbent particles that exhibit an activation time until swelling begins, which time can be varied by the coating's material and thickness. Some of the coating materials disclosed are non-reactive polysaccharides such as gelatin, microcrystalline cellulose and cellulose derivatives. The activation period to the start of swelling should be at least 5, preferably 15 and more strongly preferred, 60 minutes.

Coated superabsorbent polymers have the disadvantage that even a small initial wetting, without necessarily leading to the swelling of the highly swellable polymers, leads to a destruction of the surface treatment by dissolution, detachment, swelling or decomposition. Once the coating around the polymers has dissolved, such superabsorbent polymers exhibit the high swelling rate of a conventional material without surface treatment. Thus the desired effect of improved liquid management in the absorbent material is lost.

It is therefore an object of the present invention to provide an absorbing polymer composition that exhibits improved delayed free water absorption, as well as maintaining excellent properties such as capabilities of maintaining high liquid permeability and liquid retention even when the superabsorbent polymer is increased in percent by weight based on the absorbent structure.

SUMMARY OF THE INVENTION

The present invention is directed to a coated superabsorbent polymer particulate comprising a coated superabsorbent polymer particulate wherein the coated superabsorbent polymer particulate has a delayed free water absorption property of absorbing less than about 13 grams of water per gram of superabsorbent polymer in about 15 seconds.

The present invention is further directed to a coated superabsorbent polymer particulate having improved delayed free water absorption comprising a) a composition comprising from about 55 to about 99.9 wt. % of polymerizable unsaturated acid group containing monomers; and from about 0.001 to about 5.0 wt. % of internal crosslinking agent; wherein the composition has a degree of neutralization of more than about 20%; and b) a salt coated on the composition wherein the coated superabsorbent polymer has a delayed free water absorption of absorbing less than about 13 grams of water per gram of superabsorbent polymer in about 15 seconds.

The present invention is also directed to a method of preparing a coated superabsorbent polymer having a delayed free water absorption property of absorbing less than about 13 grams of water per gram of superabsorbent polymer in about 15 seconds, the method comprising the steps of a) a composition comprising from about 55 to about 99.9 wt. % of polymerizable unsaturated acid group containing monomers; and b) from about 0.001 to about 5.0 wt. % of internal crosslinking agent; c) and a neutralizing agent wherein the composition has a degree of neutralization of more than about 20%; and d) initiating free radical polymerization by adding an effective amount of at least one free radical initiator and polymerizing at temperatures ranging from about 0° C. to about 100° C. to form a microcellular hydrogel; and e) drying said gel pieces at temperatures ranging from about 85° C. to about 210° C. to form dry pieces, which dry pieces, are ground to a size of from about 0.05 mm to about 5.0 mm diameter to form an improved dry superabsorbent polymer; and f) adding to the dried superabsorbent polymer particulate a coating composition to coat the superabsorbent polymer particulate.

DESCRIPTION OF THE PREFERRED EMBODIMENTS

A suitable superabsorbent polymer may be selected from natural, biodegradable, synthetic and modified natural polymers and materials. The term crosslinked used in reference to the superabsorbent polymer refers to any means for effectively rendering normally water-soluble materials substantially water-insoluble but swellable. Such a crosslinking means can include for example, physical entanglement, crystalline domains, covalent bonds, ionic complexes and associations, hydrophilic associations such as hydrogen bonding, hydrophobic associations or Van der Waals forces. Superabsorbent polymers include internal crosslinking and surface crosslinking.

Specifically, Applicants have discovered a coated superabsorbent polymer having improved delayed free water absorption obtained by the addition of a specific coating to the superabsorbent polymer particulate. In particular, the present invention is directed to a coated superabsorbent polymer particulate comprising a coated superabsorbent polymer particulate having a delayed free water absorption property of absorbing about 13 grams or less of water per gram of superabsorbent polymer in about 15 seconds; or absorbing 10 grams or less of water per gram of superabsorbent polymer in about 15 seconds; or, absorbing 8 grams or less of water per gram of superabsorbent polymer in about 15 seconds; or absorbing 5 grams or less of water per gram of superabsorbent polymer in about 15 seconds; or absorbing 3 grams or less of water per gram of superabsorbent polymer in about 15 seconds.

The coated superabsorbent polymer particulate of the present invention includes coatings selected from a group consisting of monovalent salts, divalent salts, trivalent salts and higher salts; or, the coating is selected from the group consisting of calcium chloride, sodium chloride, potassium chloride, calcium nitrate, magnesium chloride, aluminum sulfate, aluminum chloride and ferric chloride.

The present invention is further directed to a coated superabsorbent polymer having improved delayed water absorption comprising a) a composition comprising from about 55 to about 99.9 wt. % of polymerizable unsaturated acid group containing monomers; and from about 0.001 to about 5.0 wt. % of internal crosslinking agent; wherein the composition has a degree of neutralization of more than about 20%; and b) a salt coated on the composition wherein the coated superabsorbent polymer has a delayed free water absorption property of absorbing about 13 grams or less of water per gram of superabsorbent polymer in about 15 seconds.

The present invention is also directed to a method of preparing a coated superabsorbent polymer having improved delayed free water absorption comprising the steps of a) a composition comprising from about 55 to about 99.9 wt. % of polymerizable unsaturated acid group containing monomers; and b) from about 0.001 to about 5.0 wt. % of internal crosslinking agent; c) and a neutralizing agent wherein the composition has a degree of neutralization of more than about 20%; and d) initiating free radical polymerization by adding an effective amount of at least one free radical initiator and polymerizing at temperatures ranging from about 0° C. to about 100° C. to form a microcellular hydrogel; and e) drying said gel pieces at temperatures ranging from about 85° C. to about 210° C. to form dry pieces, which dry pieces, are ground to a size of from about 0.05 mm to about 5.0 mm diameter to form an improved dry superabsorbent polymer; and f) adding to the dried gel pieces a coating composition to coat the polymer gel pieces.

The timing of free water absorption of the inventive superabsorbent polymer is referred to as delayed, reduced, or slower, as it is intended to mean the free water absorption in a short amount of time, i.e., about 1 minute or more. This is distinguished from free water absorption where the superabsorbent polymer is allowed to absorb water until no more water can be absorbed, which typically is 3 to 5 minutes, and is called the ultimate free water absorption as a reference to the total amount of water absorbed regardless of how long that takes.

The superabsorbent polymer of the present invention is obtained by the initial polymerization of from about 55 to about 99.9 wt. % of polymerizable unsaturated acid group containing monomers. Suitable monomers include those containing carboxyl groups, such as acrylic acid, methacrylic acid or 2-acrylamido-2-methylpropanesulfonic acid, or mixtures of these monomers are preferred here. It is preferable for at least about 50-wt. %, and more preferably at least about 75 wt. % of the acid groups to be carboxyl groups. The acid groups are neutralized to the extent of at least about 25 mol %, preferably 25 mol % to 80 mol %, that is the acid groups are present in salt form. It is preferred to obtain polymers obtained by polymerization of acrylic acid or methacrylic acid, the carboxyl groups of which are neutralized to the extent of 50-80-mol %, in the presence of internal crosslinking agents.

Further monomers, which can be used for the preparation of the absorbent polymers according to the invention, are from 0 to about 40 wt. % of ethylenically unsaturated monomers which can be copolymerized with a), such as e.g. acrylamide, methacrylamide, hydroxyethyl acrylate, dimethylaminoalkyl (meth)-acrylate, ethoxylated (meth)-acrylates, dimethylaminopropylacrylamide or acrylamidopropyltrimethylammonium chloride. More than 40 wt. % of these monomers can impair the swellability of the polymers.

The superabsorbent polymer of the present invention further includes from about 0.001 to about 5.0 wt. % of internal crosslinking agent. The internal crosslinking agent has at least two ethylenically unsaturated double bonds or one ethylenically unsaturated double bond and one functional group which is reactive towards acid groups of the polymerizable unsaturated acid group containing monomers or several functional groups which are reactive towards acid groups can be used as the internal crosslinking component and which is present during the polymerization of the polymerizable unsaturated acid group containing monomers.

Examples of internal crosslinking agents include aliphatic unsaturated amides, such as methylenebisacryl- or -methacrylamide or ethylenebisacrylamide, and furthermore aliphatic esters of polyols or alkoxylated polyols with ethylenically unsaturated acids, such as di(meth)acrylates or tri(meth)acrylates of butanediol or ethylene glycol, polyglycols or trimethylolpropane, di- and triacrylate esters of trimethylolpropane which is preferably oxyalkylated, preferably ethoxylated, with 1 to 30 mol of alkylene oxide, acrylate and methacrylate esters of glycerol and pentaerythritol and of glycerol and pentaerythritol oxyethylated with preferably 1 to 30 mol of ethylene oxide and furthermore allyl compounds, such as allyl (meth)acrylate, alkoxylated allyl (meth)acrylate reacted with preferably 1 to 30 mol of ethylene oxide, triallyl cyanurate, triallyl isocyanurate, maleic acid diallyl ester, poly-allyl esters, tetraallyloxyethane, triallylamine, tetraallylethylenediamine, diols, polyols, hydroxy allyl or acrylate compounds and allyl esters of phosphoric acid or phosphorous acid, and furthermore monomers which are capable of crosslinking, such as N-methylol compounds of unsaturated amides, such as of methacrylamide or acrylamide, and the ethers derived there from. Ionic crosslinkers such as multivalent metal salts may also be employed. Mixtures of the crosslinking agents mentioned can also be employed. The content of the internal crosslinking agents is from about 0.01 to about 5 wt. %, and preferably from about 0.1 to about 3.0 wt. %, based on the total amount of the polymerizable unsaturated acid group containing monomers.

The usual initiators, such as e.g. azo or peroxo compounds, redox systems or UV initiators, (sensitizers), and/or radiation are used for initiation of the free-radical polymerization.

The coated absorbent polymers according to the present invention include from about 0.5 to about 20 wt % of a salt for a coating. The coating is selected from a group consisting of monovalent salts, divalent salts, trivalent salts and higher salts; or is selected from the group consisting of calcium chloride, sodium chloride, potassium chloride, calcium nitrate, magnesium chloride, aluminum sulfate, aluminum chloride and ferric chloride. Mixtures of metal salts can be employed.

The polymer and salt suitably are mixed by dry blending, or preferably in solution, using means well known to those skilled in the art. Aqueous solutions are preferred. With dry blending, a binder may be employed in an amount which is sufficient to ensure that a substantially uniform mixture of the coating and the superabsorbent polymer is maintained.

The absorbent polymers may be surface crosslinked after polymerization. Surface crosslinking is any process that increases the crosslink density of the polymer matrix in the vicinity of the superabsorbent particle surface with respect to the crosslinking density of the particle interior. The absorbent polymers are typically surface crosslinked by the addition of a surface crosslinking agent. Preferred surface crosslinking agents include chemicals with one or more functional groups, which are reactive towards pendant groups of the polymer chains, typically the acid groups. The content of the surface crosslinking agents is preferably from about 0.01 to about 5 wt. %, and may be from about 0.1 to about 3.0 wt. %, based on the weight of the dry polymer. A heating step is preferred after addition of the surface crosslinking agent.

While particles are then used by way of example of the physical form of superabsorbent polymers, the invention is not limited to this form and is applicable to other forms such as fibers, foams, films, beads, rods and the like.

The superabsorbent polymers may also include from 0 to about 30 wt. % of water-soluble polymers, such as partly or completely hydrolysed polyvinyl acetate, polyvinylpyrrolidone, starch or starch derivatives, polyglycols or polyacrylic acids, preferably in polymerized-in form. The molecular weight of these polymers is not critical as long as they are water-soluble. Preferred water-soluble polymers are starch and polyvinyl alcohol. The preferred content of such water-soluble polymers in the absorbent polymer according to the invention is 0-30 wt. %, preferably 0-5 wt. %, based on the total amount of components. The water-soluble polymers, preferably synthetic polymers, such as polyvinyl alcohol, can also serve as a graft base for the monomers to be polymerized.

Further additives of the superabsorbent polymers according to the invention may optionally be employed, such as odor-binding substances, such as cyclodextrins, zeolites, inorganic or organic salts and similar materials; anti-caking additives, flow modification agents and the like.

The polymers according to the invention are preferably prepared by two methods. The polymers can be prepared continuously or discontinuously in a large-scale industrial manner by the abovementioned known process, the after-crosslinking according to the invention being carried out accordingly.

According to the first method, the partly neutralized monomer, preferably acrylic acid, is converted into a gel by free-radical polymerization in aqueous solution in the presence of crosslinking agents and optionally further components, and the gel is comminuted, dried, ground and sieved off to the desired particle size. This solution polymerization can be carried out continuously or discontinuously.

Inverse suspension and emulsion polymerization can also be used for preparation of the products according to the invention. According to these processes, an aqueous, partly neutralized solution of monomers, preferably acrylic acid, is dispersed in a hydrophobic, organic solvent with the aid of protective colloids and/or emulsifiers and the polymerization is started by free radical initiators. The internal crosslinking agents either are dissolved in the monomer solution and are metered in together with this, or are added separately and optionally during the polymerization. The water is then removed azeotropically from the mixture and the polymer is filtered off and optionally dried. Internal crosslinking can be carried out by polymerizing-in a polyfunctional crosslinking agent dissolved in the monomer solution and/or by reaction of suitable crosslinking agents with functional groups of the polymer during the polymerization steps.

Especially, the inventive superabsorbent polymers, due to their free water absorption characteristics, are very useful in a wet-laid process for manufacturing a wet-laid web, having a superabsorbent polymer component mixed with a fibrous component and useful as a core composite in a sanitary article. Examples of the wet-laid process are described in the above-mentioned published European Patent Application No. 0 437 816 A1 and U.S. Pat. No. 4,605,401. As the wet-laid process involves mixing an aqueous slurry of superabsorbent polymer with fiber, water is absorbed during the wet-laid process. Consequently, at the end of the wet-laid process, the wet-laid web must be dried prior to placing it as a core composite in an end use article, such as a disposable diaper.

By employing the superabsorbent polymers of the present invention, less water should be absorbed during the wet-laid process of making a web. Thus, there should be less water to remove during drying, resulting in a shorter drying time for the wet web, which is very advantageous in a large-scale factory production setting.

Moreover, after drying of the wet-laid web, due to the free water absorbency characteristics of the superabsorbent polymer, the web will have an improved solids content, as compared to a wet-laid web containing prior art superabsorbent polymer. Typically, the inventive wet-laid web will have a solids content above about 18%.

In one embodiment, the superabsorbent polymer is used in the form of discrete particles. Superabsorbent polymer particles can be of any suitable shape, for example, spiral or semi-spiral, cubic, rod-like, polyhedral etc. Particle shapes having a large greatest dimension/smallest dimension ratio, like needles, flakes or fibers are also contemplated for use herein.

TEST METHODS

The methods for performing the vortex time swell rate test. Unless otherwise stated, the test fluid used in all the test methods described below is an aqueous 0.9 wt. % sodium chloride solution, such as that available from Ricca Chemical Company (Arlington, Tex.). Unless otherwise stated, all tests were conducted at about 70 degrees Fahrenheit and between 10 and 60% relative humidity.

To characterize the superabsorbent polymers as set out in the Laboratory Examples below (both those superabsorbent polymers of the present invention, as well as those comparison, superabsorbent polymers), the centrifuge retention capacity (CRC), the absorbency under load (AUL), and the free water absorption (FWA) were measured in the following manner.

Centrifuge Retention Capacity (CRC) Test. The test was conducted at ambient conditions of room temperature. Retention of 0.9% saline solution was determined according to the tea bag test method and reported as an average value of 2 measurements. Approximately 200 mg of SAP particles, that had been sieved to a particle size distribution ranging from about 300 to 600 micrometers, were enclosed in a tea bag and immersed in the saline solution for 30 minutes. Next, the tea bag was centrifuged at 1600 rpm for 3 minutes and weighed. The diameter of the centrifuge apparatus was about 20 cm. Also, 2 tea bags without particles were used as blanks.

The specific procedure is as follows:
1. Cut the teabag stock into 3×5-inch rectangles. Fold the strips in half, and seal two of the three open sides so the inside edge of the seals are about ¼ inch from the edge of the teabag.

2. For each determination, weigh 0.200+/−0.005 grams of SAP into a teabag. Record the initial weight as $W_1$.
3. Seal the open side of the teabags using the heat sealer. Store the teabags in a desiccator if the period of time between the initial weighing and the determination is greater than 30 minutes.
4. Prepare the two test method blanks by heat-treating two empty teabags without the SAP sample.
5. Fill a dish with 0.9% saline solution to approximately 4 cm high.
6. Prepare the sealed teabags for immersion by gently shaking the sample to distribute the SAP particles evenly across the teabag.
7. Immerse the teabags in the 0.9% saline.
8. After 30 minutes, remove the teabags from the test liquid.
9. Place the teabags into the centrifuge making sure to balance the centrifuge with proper teabag placement. Centrifuge for 3 minutes at 1600 rpm.
10. After centrifugation, determine the weights of each sample. Record the weights of the test blanks, without test sample ($W_2$) and the weight of the teabag with test sample accurate to 0.01($W_3$).

Then, the CRC property (measured in grams of liquid absorbed per gram of particles) was calculated according to the following equation.

$$CRC = (W_3 - W_2 - W_1)W_1$$

where:
CRC=retention after 30 minutes immersion time (g/g)
$W_1$=initial weight in grams of SAP particles
$W_2$=average weight in grams of two blanks after centrifugation
$W_3$=weight in grams of test tea bag after centrifugation Absorbency Under Load (AUL)

The ability of a superabsorbent material to absorb a liquid while under a load is determined as follows. The AUL measuring system is comprised of: 1) a Plexiglas cylinder with beveled edges of dimension, inner diameter=25 mm; height=33 mm and fitted with a 400-mesh (36 microns) size metal screen on bottom; 2) a plastic spacer (diameter=24+/−1 mm; weight=5.20+/−0.015 g); 3) a stainless steel weight (diameter=24+/−1 mm; weight=98.35+/−0.05 g for 0.3 psi pressure AUL measurement and 315.3+/−0.09 g for 0.9 psi pressure AUL measurement); 4) a fritted disc (from Knotes Glass, Catalogue number 9520001223); 5) a round filter paper (Whatman 3); 6) a petri dish (diameter=150 mm; height=20 mm); 7) an analytical balance (accurate to 0.001 grams); and 8) a stop watch.

The general AUL measurement procedure is as follows:
1. Place the fritted disc in the Petri dish. Note that fritted discs to be used in testing need to have been soaking in sodium chloride solution for a minimum of one hour prior to test use.
2. Add 0.9% sodium chloride solution to the Petri dish so that the solution is slightly below the top of the fritted disc.
3. Place the filter paper on the top of the fritted disc, thoroughly wetting the filter paper with sodium chloride solution, avoiding any supernatant liquid.
4. Tare the cylinder on top-loading balance. Evenly distribute 0.160+/−0.005 grams of SAP sample on to the metal screen of a clean and dry Flexiglas cylinder. Record actual weight of SAP sample, (SA).
5. Care place the plastic spacer followed by the appropriate stainless steel weight into the cylinder. Record the weight of the completed apparatus, (A).
6. Place the AUL apparatus on the damp filter paper, allowing the apparatus to absorb for 1 hour. Maintain the sodium chloride solution level to slightly below the top surface of fritted disc throughout entire test period.
7. Reweigh the AUL apparatus after 1 hour and record weight, (B). Calculation:

$$0.3 \text{ or, } 0.9 \text{ psi } AUL\ (g/g) = (B-A)/SA$$

where, A=dry weight of AUL apparatus with SAP
B=weight of AUL apparatus with SAP after 1 hour absorbing Free Water Absorption 15 second ($FWA_{15sec}$) Test. To determine the SAP's free water absorption, a vacuum apparatus was assembled. More specifically, a vacuum pump was attached, by Tygon tubing, to a vacuum flask, atop which was positioned the bottom portion of a Buchner funnel, which was sealed properly to the flask using a one-hole rubber stopper. A magnetic stirrer was placed beside the apparatus. After assemblage of the apparatus, the vacuum pump was engaged and allowed to stay on throughout all $FWA_{15sec}$ testing.

Using a 250 ml graduated cylinder, 150 ml.+/−0.1 ml of 23.0° C. +/−0.0.5.degree. Tap water was measured into a 250 ml beaker containing a 1-inch stir bar. The beaker of water was placed on a stir plate and allowed to stir so that the created vortex ended approximately 2 to 3 cm from the surface of the liquid.

A dry 80 mesh (180 micrometer) sieve was weighted and placed on top of the funnel apparatus, and the vacuum pump was then turned on. The sieve was pressed down until the sieve was tightly anchored to the funnel through suction. About 3.00+/−0.05 g SAP was weighed in an aluminum dish. The weighed SAP was then poured into the vortex of the stirring water and a stopwatch was started simultaneously. Stirring was then continued for 15 seconds after which the wet polymer was immediately filtered under a constant vacuum of 5 inches Hg. Care was taken so that the wet SAP transfer time was not more than an additional 3 seconds. The sieve with SAP was kept under vacuum suction for 30 seconds. Then the sieve was removed from the vacuum funnel and the underside of the sieve was wiped with a paper towel to remove any residual water that might be present. The sieve with wet-SAP was then weighed. The weight of the dry sieve was subtracted from this weight to determine the weight of the wet-SAP.

Then, the $FWA_{15sec}$ (g of liquid absorbed/g of SAP) was calculated from the gel weight according to the following equation.

$$FWA_{15sec}\ (g/g) = (g\ Gel\ Weight - g\ SAP)/(g\ SAP)$$

EXAMPLES

The present invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

General Procedure for Making Coated Superabsorbent Polymer The following general procedure was used in the following examples. A solution of desired coating of a salt of concentration ranging from 20-50 wt. % was prepared by stirring the salt in de-ionized water at room temperature. An aliquot of 50-200 g of a commercial dry superabsorbent polymer was placed in a mixing bowl. The mixer was set at a high speed. A calculated amount of previously prepared aqueous salt solution was sprayed by an air-brush while the particulate superabsorbent polymer was vigorously agitated. The salt coated superabsorbent polymer particles were either dried in a convection oven at 100° C. for about 1 hour or allowed to relax at room temperature for 12-24 hours. Then, the properties of the coated superabsorbent polymer, including the $FWA_{15sec}$, CRC, $AUL_{0.3psi}$ and $AUL_{0.9psi}$, were determined according to the tests provided herein.

Example 1

(Coating with NaCl) About 50 g of Stockhausen SXM-71 superabsorbent polymer was sprayed with 20 g of 25 wt % aqueous NaCl solution using the procedure described above. The coated polymer was dried in a convection oven at 100° C. for 1 hour. The dried polymer was ground and sieved between 20 and 100 standard mesh size screens. The properties were then measured and are included in Table 1.

Comparative Example 1 (Comp Ex 1)

Same as Example 1 except the SAP is not coated.

Example 2

(Coating with KCl) About 50 g of Stockhausen SXM-71 superabsorbent polymer was sprayed with 16.67 g of 30 wt % aqueous KCl solution using the procedure described above. The coated polymer was dried in a convection oven at 100° C. for 1 hour. The dried polymer was ground and sieved between 20 and 100 standard mesh size screens. The properties were then measured and are included in Table 1.

Two aliquots of 50 g of Stockhausen SXM-77 superabsorbent polymer was sprayed with 20 g and 40 g respectively of 25 wt % aqueous KCl solution using the procedure described above. The coated polymer was dried in a convection oven at 100° C. for 1 hour. The dried polymer was ground and sieved between 20 and 100 standard mesh size screens. The properties were then measured and are included in Table 1.

Comparative Example 2 (Comp Ex 2)

Same as Example 2 except the SAP is not coated.

Example 3

(Coating with $CaCl_2$) About 200 g of Stockhausen SXM-71 superabsorbent polymer was sprayed with 8 g of 25 wt % aqueous $CaCl_2$ solution using the procedure described above. The coated polymer was dried in a convection oven at 100° C. for 1 hour. The dried polymer was ground and sieved between 20 and 100 standard mesh size screens. The properties were then measured and are included in Table 1.

About 50 g of Stockhausen SXM-71 superabsorbent polymer was sprayed with 10 g of 25 wt % aqueous $CaCl_2$ solution using the procedure described above. The coated polymer was dried in a convection oven at 100° C. for 1 hour. The dried polymer was ground and sieved between 20 and 100 standard mesh size screens. The properties were then measured and are included in Table 1.

About 50 g of Stockhausen SXM-77 superabsorbent polymer was sprayed with 2 g of 25 wt % aqueous $CaCl_2$ solution using the procedure described above. Similarly, 100 g of SXM-77 was sprayed with 8 g of the same $CaCl_2$ solution. The coated polymer was dried in a convection oven at 100° C. for 1 hour. The dried polymer was ground and sieved between 20 and 100 standard mesh size screens. The properties were then measured and are included in Table 1.

Comparative Example 3 (Comp Ex 3)

Same as Example 3 except the SAP is not coated.

Example 4

(Coating with $Ca(NO_3)_2$) Aliquots of 50 g of Stockhausen SXM-71 superabsorbent polymer was sprayed with 2-10 g of 50 wt % aqueous $Ca(NO_3)_2$ solutions using the procedure described above. The coated polymer was dried in a convection oven at 100° C. for 1 hour. The dried polymer was ground and sieved between 20 and 100 standard mesh size screens. The properties were then measured and are included in Table 1.

Comparative Example 4 (Comp Ex 4)

Same as Example 4 except the SAP is not coated.

Example 5

(Coating with $MgCl_2$) About 50 g aliquots of Stockhausen SXM-71 superabsorbent polymer were sprayed with 2-10 g of 50 wt % aqueous $MgCl_2$ solution using the procedure described above. The coated polymer was dried in a convection oven at 100° C. for 1 hour. The dried polymer was ground and sieved between 20 and 100 standard mesh size screens. The properties were then measured and are included in Table 1.

About 50 g aliquots of Stockhausen SXM-71 and SXM-880 superabsorbent polymer were sprayed with 1-5 g of 50 wt % aqueous $MgCl_2$ solution using the procedure described above. The coated polymer was dried in a convection oven at 100° C. for 1 hour. The dried polymer was ground and sieved between 20 and 100 standard mesh size screens. The properties were then measured and are included in Table 1.

Comparative Example 5 (Comp Ex 5)

Same as Example 5 except the SAP is not coated.

Example 6

(Coating with $Al_2(SO_4)_3$) About 50 g aliquots of Stockhausen SXM-71 superabsorbent polymer was sprayed with 2-10 g of 50 wt % aqueous $Al_2(SO_4)_3 \cdot xH_2O$ solution using the procedure described above. The coated polymer was dried in a convection oven at 100° C. for 1 hour. The dried polymer was ground and sieved between 20 and 100 standard mesh size screens. The properties were then measured and are included in Table 1.

Comparative Example 6 (Comp Ex 6)

Same as Example 4 except the SAP is not coated.

Example 7

(Coating with $AlCl_3$) About 50 g aliquots of Stockhausen SXM-71 superabsorbent polymer was sprayed with 2-10 g of 50 wt % aqueous $AlCl_3$ solution using the procedure described above. The coated polymer was dried in a convection oven at 100° C. for 1 hour. The dried polymer was ground and sieved between 20 and 100 standard mesh size screens. The properties were then measured and are included in Table 1.

Comparative Example 7 (Comp Ex 7)

Same as Example 7 except the SAP is not coated.

Example 8

(Coating with $FeCl_3 \cdot 6H_2O$) About 50 g aliquots of Stockhausen SXM-71 superabsorbent polymer was sprayed with 4-10 g of 25 wt % aqueous $FeCl_3 \cdot 6H_2O$ solutions using the procedure described above. The coated polymer was dried in a convection oven at 100° C. for 1 hour. The dried polymer was ground and sieved between 20 and 100 standard mesh size screens. The properties were then measured and are included in Table 1.

Comparative Example 8 (Comp Ex 8) Same as Example 8 except the SAP is not coated.

TABLE 1

Effect of Coatings on SAPs

| Example | SAP | Coating % wt/wt | $FWA_{15sec}$ (g/g) | % Reduction FWA | CRC (g/g) | $AUL_{0.3psi}$ (g/g) | $AUL_{0.9psi}$ (g/g) |
|---|---|---|---|---|---|---|---|
| Comp Ex 1 | SXM71 | none | 8.6 | — | 35.2 | 31.6 | 20.7 |
| Example 1 | SXM71 | 10% | 4.7 | 45.3 | 29.1 | 22.4 | 13.7 |
| Comp Ex 2 | SXM71 | none | 8.6 | — | 35.2 | 31.6 | 20.7 |
| Comp Ex 2 | SXM77 | none | 16.1 | — | 41.9 | 33.9 | 24.6 |
| Example 2 | SXM71 | 10 | 5.2 | 39.5 | 30.6 | 23.9 | 14.7 |
| Example 2 | SXM77 | 10 | 10.5 | 34.5 | 29.5 | 25.5 | 16.3 |
| Example 2 | SXM77 | 20 | 7.1 | 56 | 26.2 | 21.2 | 14.6 |
| Comp Ex 3 | SXM71 | none | 8.6 | — | 35.2 | 31.6 | 20.7 |
| Comp Ex 3 | SXM77 | none | 16.1 | — | 41.9 | 33.9 | 24.6 |
| Comp Ex 3 | SXM800 | none | 10.4 | — | 30.3 | 29.7 | 21 |
| Example 3 | SXM71 | 1 | 1.5 | 83 | 33 | 30 | 19.4 |
| Example 3 | SXM71 | 5 | 0.7 | 92 | 34.6 | 25.1 | 17.4 |
| Example 3 | SXM77 | 1 | 5.1 | 68 | 33.9 | 31.4 | 21.3 |
| Example 3 | SXM77 | 2 | 3.2 | 80 | 34.4 | 31.2 | 17.6 |
| Example 3 | SXM880 | 1 | 4.6 | 56 | 28.4 | 28.7 | 19.9 |
| Example 3 | SXM880 | 5 | 2.8 | 73 | 25.3 | 23.7 | 16.9 |
| Comp Ex 4 | SXM71 | none | 8.6 | — | 35.2 | 31.6 | 20.7 |
| Example 4 | SXM71 | 2 | 1.7 | 80 | 31.4 | 36.5 | 17.7 |
| Example 4 | SXM71 | 5 | 0.8 | 91 | 28.3 | 23.4 | 16.1 |
| Example 4 | SXM71 | 10 | 0.5 | 94 | 26.9 | 21.8 | 13.8 |
| Comp Ex 5 | SXM71 | none | 8.6 | — | 35.2 | 31.6 | 20.7 |
| Comp Ex 5 | SXM77 | none | 16.1 | — | 41.9 | 33.9 | 24.6 |
| Comp Ex 5 | SXM880 | none | 10.4 | — | 30.3 | 29.7 | 21.0 |
| Example 5 | SXM71 | 1 | 3.0 | 65 | 32.9 | 28.0 | 17.3 |
| Example 5 | SXM77 | 2 | 2.8 | 67 | 31.7 | 26.5 | 16.8 |
| Example 5 | SXM880 | 5 | 1.6 | 81 | 28.8 | 22.9 | 16.2 |
| Example 5 | SXM71 | 1 | 12.4 | 23 | 34.4 | 31.6 | 19.0 |
| Example 5 | SXM77 | 2 | 8.0 | 50 | 34.4 | 32.0 | 19.4 |
| Example 5 | SXM880 | 5 | 7.0 | 57 | 31.3 | 29.5 | 18.0 |
| Example 5 | SXM71 | 1 | 5.7 | 45 | 30.4 | 29.7 | 22.6 |
| Example 5 | SXM77 | 2 | 4.4 | 58 | 29.0 | 28.4 | 21.2 |
| Example 5 | SXM880 | 5 | 3.6 | 65 | 27.4 | 26.2 | 20.0 |
| Comp Ex 6 | SXM71 | none | 8.6 | — | 35.2 | 31.6 | 20.7 |
| Example 6 | SXM71 | 2 | 8.1 | 6 | 33.7 | 26.8 | 17.3 |
| Example 6 | SXM71 | 5 | 5.7 | 36 | 32.4 | 25.8 | 16.2 |
| Comp Ex 7 | SXM71 | none | 8.6 | — | 35.2 | 31.6 | 20.7 |
| Example 7 | SXM71 | 2 | 5.0 | 42 | 34.1 | 25.5 | 14.2 |
| Example 7 | SXM71 | 5 | 3.5 | 59 | 32.9 | 23.0 | 13.7 |
| Comp Ex 8 | SXM71 | none | 8.6 | — | 35.2 | 31.6 | 20.7 |
| Example 8 | SXM71 | 2 | 3.4 | 60 | 34.5 | 21.9 | 13.4 |
| Example 8 | SXM71 | 5 | 1.5 | 83 | 33.6 | 19.4 | 12.5 |

Example 9

Washing Experiments

The coated superabsorbent polymer was exposed to water as described in the method for 15-second FWA determination. The wet polymer was filtered under vacuum and then heated in a convection oven at 100° C. to dryness. Then the performance characteristics were again determined. The results are given in Table 2.

TABLE 2

| | SAP | Treatment | $FWA_{15sec}$ | CRC | $AUL_{0.3psi}$ | $AUL_{0.9psi}$ |
|---|---|---|---|---|---|---|
| 9-1 | SXM71 | 1% $CaCl_2$ | 1.9 | 30.4 | 30 | 20 |
| 9-2 | 9-1 | Washed & Dried | 6.6 | 32.9 | 27.1 | 14.2 |
| 9-3 | SXM71 | 1% $CaCl_2$ | 1.5 | 33.0 | 30.0 | 19.4 |
| 9-4 | 9-3 | Washed & Dried | 6.3 | 28 | 28.5 | 16.9 |
| 9-5 | SXM71 | 1% $Ca(NO_3)_2$ | 2.5 | 31 | 27.5 | 17.9 |
| 9-6 | 9-5 | Washed & Dried | 7.2 | 31.9 | 23.7 | 11.6 |
| 9-7 | SXM71 | 1% $MgCl_2$ | 3.0 | 32.9 | 28 | 17.3 |
| 9-8 | 9-7 | Washed & Dried | 5.7 | 32.9 | 25 | 11.2 |

What is claimed:

1. A coated superabsorbent polymer particulate comprising
    a) a superabsorbent polymer particulate comprising from about 55 to about 99.9 wt. % of polymerizable unsaturated acid group containing monomers; and
    from about 0.001 to about 5.0 wt % of internal crosslinking agent based on the polymerizable unsaturated acid group containing monomer; wherein the composition has a degree of neutralization of more than 25 mole %; and
    b) from about 0.5 to about 20 wt % of a coating containing salt selected from a group consisting of monovalent salts, divalent salts, trivalent salts and higher salts on the superabsorbent polymer particulate surface;
    wherein the coated superabsorbent polymer particulate has a water absorption property of absorbing about 3.6 grams or less of water per gram of superabsorbent polymer in about 15 seconds according to the Free Water Absorption 15 second ($FWA_{15sec}$) Test, and wherein when the coating of (b) is washed off the superabsorbent polymer particulate of (a), the resulting superabsorbent polymer particulate has a water absorption property of absorbing from about 5.7 grams to about 7.2 grams of water per gram of superabsorbent polymer in about 15 seconds according to the Free Water Absorption 15 second ($FWA_{15sec}$) Test.

2. The coated superabsorbent polymer particulate of claim 1 having a water absorption property of absorbing about 3 grams or less of water per gram of superabsorbent polymer in about 15 seconds according to the Free Water Absorption 15 second ($FWA_{15sec}$) Test.

3. The coated superabsorbent polymer particulate of claim 1 having a water absorption property of absorbing about 1.5 gram or less of water per gram of superabsorbent polymer in about 15 seconds according to the Free Water Absorption 15 second ($FWA_{15sec}$) Test.

4. The coated superabsorbent polymer particulate of claim 1 having a water absorption property of absorbing about 3 grams or less of water per gram of superabsorbent polymer in about 15 seconds according to the Free Water Absorption 15 second ($FWA_{15sec}$) Test and a centrifuge retention capacity of retaining 28 grams or more of aqueous saline per gram of superabsorbent polymer.

5. The coated superabsorbent polymer particulate of claim 1 wherein the salt is selected from the group consisting of calcium chloride, sodium chloride, potassium chloride, calcium nitrate, magnesium chloride, aluminum sulfate, aluminum chloride, and ferric chloride.

6. The coated superabsorbent polymer particulate of claim 1 having a water absorption property of absorbing about 3 grams or less of water per gram of superabsorbent polymer in about 15 seconds according to the Free Water Absorption 15 second ($FWA_{15sec}$) Test and having an absorbency under load at 0.9 psi of retaining more than 13 grams of aqueous saline per gram of superabsorbent polymer.

7. A coated surface crosslinked superabsorbent polymer composition comprising a superabsorbent polymer comprising:
    a) from about 55% to about 99.9% by weight of the superabsorbent polymer of polymerizable unsaturated acid group containing monomer based on the superabsorbent polymer; and
    b) from about 0.001% to about 5% by weight of internal crossliniking agent based on the polymerizable unsaturated acid group containing monomer; wherein the superabsorbent polymer has a degree of neutralization of greater than 25%; wherein elements a) and b) are polymerized and prepared into superabsorbent polymer particles; further comprising on the surface of the superabsorbent polymer particles
    (c) from about 0.01% to about 5% by weight of surface crosslinking agent based on the dry superabsorbent polymer particulate to form surface crosslinked superabsorbent polymer particles; and
    (d) from about 0.5 to about 20 wt. % by weight of a salt coating containing a salt selected from a group consisting of monovalent salts, divalent salts, trivalent salts and higher salts wherein the salt coating is coated onto the surface of the superabsorbent polymer particles;
    wherein the coated surface crosslinked superabsorbent polymer particulate has a water absorption property of absorbing about 3.6 grams or less of water per gram of superabsorbent polymer in about 15 seconds according to the Free Water Absorption 15 second ($FWA_{15sec}$) Test, and wherein when the salt coating of (d) is washed off the surface crosslinked superabsorbent polymer particulate of step (c) the resulting surface crosslinked superabsorbent polymer particulate has a water absorption property of absorbing from about 5.7 grams to about 7.2 grams of water per gram of superabsorbent polymer in about 15 seconds according to the Free Water Absorption 15 second ($FWA_{15sec}$) Test.

8. The coated surface crosslinked superabsorbent polymer composition of claim 7 wherein the coating is selected from the group consisting of calcium chloride, sodium chloride, potassium chloride, calcium nitrate, magnesium chloride, aluminum sulfate, aluminum chloride, and ferric chloride.

9. The coated surface crosslinked superabsorbent polymer composition of claim 7 having a water absorption property of absorbing about 3 grams or less of water per gram of superabsorbent polymer in about 15 seconds according to the Free Water Absorption 15 second ($FWA_{15sec}$) Test.

10. The coated surface crosslinked superabsorbent polymer composition of claim 7 having a water absorption property of absorbing about 1.5 gram or less of water per gram of superabsorbent polymer in about 15 seconds according to the Free Water Absorption 15 second ($FWA_{15sec}$) Test.

11. The coated surface crosslinked superabsorbent polymer composition of claim 7 having a centrifuge retention capacity of retaining 28 grams or more of aqueous saline per gram of superabsorbent polymer and having an absorbency under load at 0.9 psi of retaining more than 13 grams of aqueous saline per gram of superabsorbent polymer.

12. The coated surface crosslinked superabsorbent polymer composition of claim 7 having a water absorption property of absorbing about 3 grams or less of water per gram of superabsorbent polymer in about 15 seconds according to the Free Water Absorption 15 second ($FWA_{15sec}$) Test, and a centrifuge retention capacity of retaining 25 grams or more of aqueous saline per gram of superabsorbent polymer.

13. The coated surface crosslinked superabsorbent polymer composition of claim 7 having a water absorption property of absorbing about 3 grams or less of water per gram of superabsorbent polymer in about 15 seconds according to the Free Water Absorption 15 second ($FWA_{15sec}$) Test and having an absorbency under load at 0.9 psi of retaining more than 18 grams of aqueous saline per gram of superabsorbent polymer.

* * * * *

UNITED STATES PATENT AND TRADEMARK OFFICE
CERTIFICATE OF CORRECTION

PATENT NO. : 7,579,402 B2
APPLICATION NO. : 10/706569
DATED : August 25, 2009
INVENTOR(S) : Iqbal Ahmed, Angela Marie Jones and Scott J. Smith It is certified that error appears in the above-identified patent and that said Letters Patent is hereby corrected as shown below:

Column 8,
Line 22, "+/-0.0.5.degree" should read -- +/- 0.5.degree --.

Column 14,
Line 25, Claim 7 "crossliniking" should read -- crosslinking --.

Signed and Sealed this

Sixth Day of October, 2009

David J. Kappos
*Director of the United States Patent and Trademark Office*